(12) United States Patent
Petersen et al.

(10) Patent No.: US 6,201,099 B1
(45) Date of Patent: Mar. 13, 2001

(54) MULTIREACTIVITY POLYMERCAPTANS, STAR POLYMERS AND METHODS OF PREPARATION

(75) Inventors: Paul M. Petersen, Princeton; Robert D. Harlan, Somerville, both of NJ (US); Jules E. Schoenberg, Plano, TX (US)

(73) Assignee: National Starch & Chemical Investment Holding Corporation, Wilmington, DE (US)

( * ) Notice: Subject to any disclaimer, the term of this patent is extended or adjusted under 35 U.S.C. 154(b) by 0 days.

(21) Appl. No.: 09/190,156

(22) Filed: Nov. 12, 1998

(51) Int. Cl.[7] ............................. C08G 75/04; C08G 75/00
(52) U.S. Cl. ......................... 528/376; 528/374; 528/364
(58) Field of Search ..................... 528/376, 374, 528/364

(56) References Cited

U.S. PATENT DOCUMENTS

| | | | |
|---|---|---|---|
| 3,364,182 | 1/1968 | Griffith | 260/79 |
| 3,769,254 | 10/1973 | Anderson et al. | 260/33.4 PQ |
| 5,391,406 | 2/1995 | Ramharack et al. | 427/516 |
| 5,399,642 | 3/1995 | Emmons et al. | 526/224 |
| 5,416,127 | 5/1995 | Chandran et al. | 522/149 |
| 5,489,397 | 2/1996 | Bainbridge | 252/174.24 |
| 5,492,965 | 2/1996 | Emmons et al. | 524/833 |
| 5,498,675 | 3/1996 | Emmons et al. | 525/537 |
| 5,536,759 | 7/1996 | Ramharack et al. | 522/35 |
| 5,574,117 | 11/1996 | Yoshida et al. | 526/224 |
| 5,679,762 | 10/1997 | Yoshida et al. | 528/364 |
| B1 3,769,254 | 2/1985 | Anderson et al. | 524/398 |

FOREIGN PATENT DOCUMENTS

| | | | |
|---|---|---|---|
| 1645232 | 11/1966 | (DE) | C08F/20/18 |
| 0 448 224 A1 | 9/1991 | (EP) | C08F/2/38 |
| 0 449 413 A1 | 10/1991 | (EP) | C08F/2/38 |
| 0 541 272 A1 | 5/1993 | (EP) | C08F/2/38 |
| 2 294 467 | 5/1996 | (GB) | C08F/20/14 |
| 9-53059 | 2/1997 | (JP) | C09J/201/00 |
| WO 96/37520 | 11/1996 | (WO) | C08F/2/38 |

OTHER PUBLICATIONS

Schaefgen and Flory, "Synthesis of Multichain Polymers and Investigation of their Viscosities", JACS, Aug. 1948, vol. 709, pp. 2709–2718.

Morton, Helminiak, Gadkary and Bueche, Preparation and Properties of Monodisperse Branched Polystyrene, *Journal of Polymer Science*, vol. 57, pp. 471–482 (1962).

Kauder, "Thols", *Encyclopedia of Chemical Technology*, Third Edition, vol. 22, pp. 946–964.

Jérome and Teyssié, Star–Shaped Block Copolymers. IV. Emulsifying Activity in the Water–Oil Emulsions, *Journal of Applied Polymer Science*, vol. 26, 343–351 (1981).

"Branched Polymers", *Encyclopedia of Polymer Science and Engineering*, vol. 2, pp. 478–499.

Simms and Spinelli, "Recent Advances in Group Transfer Polymerization and Their Applications In Coatings", *Journal of Coatings Technology*, vol. 59, No. 752, Sep. 1987, pp. 125–131.

(List continued on next page.)

*Primary Examiner*—Duc Truong
(74) *Attorney, Agent, or Firm*—Cynthia L. Foulke; Karen G. Kaiser

(57) ABSTRACT

The present invention is directed to multireactivity polymercaptans, star-shaped copolymers and methods of preparing wherein the polymer comprises a polyvalent mercaptan core and three or more polymeric arms which extend radially from the core. The polyvalent mercaptan core comprises three or more thiol groups, wherein at least two of the thiol groups are of different reactivities, such that the core is of differential reactivity. These multifunctional thiols, which will be referred to as cores of differential reactivity, act as chain transfer agents in a free radical polymerization process.

15 Claims, 3 Drawing Sheets

OTHER PUBLICATIONS

Yuan and Di Silvestro, "Polymerization of methyl methacrylate in the presence of polyfunctional chain transfer agents", Macromol. Chem. Phys. 196, 2905–2913 (1995).

Erickson, Zimmermann, Southwick and Kübler, "Liquid Reactive Polymers for Radiation Curable High Performance PSAs", *Adhesive Age*, Nov. 1995.

Puts and Sogah, "Universal Multifunctional Initiator Containing Orthogonal Reactive Sites . . . " *Macromolecules* 1997, 30, 7501–7055.

Ullisch and Burchard, "Branching in Free Radical Polymerization Due to Chain Transfer . . . ", *Makromol. Chem.*, 178, 1427–1437 (1977).

European Coatings Journal, vol. 1–2/98, p. 87.

Gia et al., "Star-shaped block copolymers. II. Microemulsions stabilizers", Colloid & Polymer Science 257, 1294–1296 (1979).

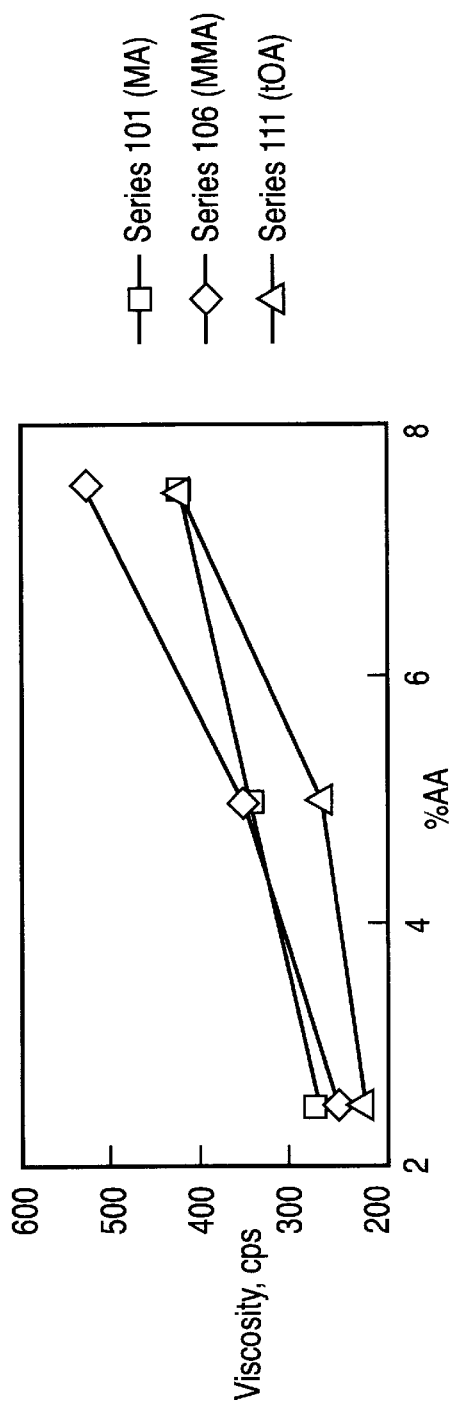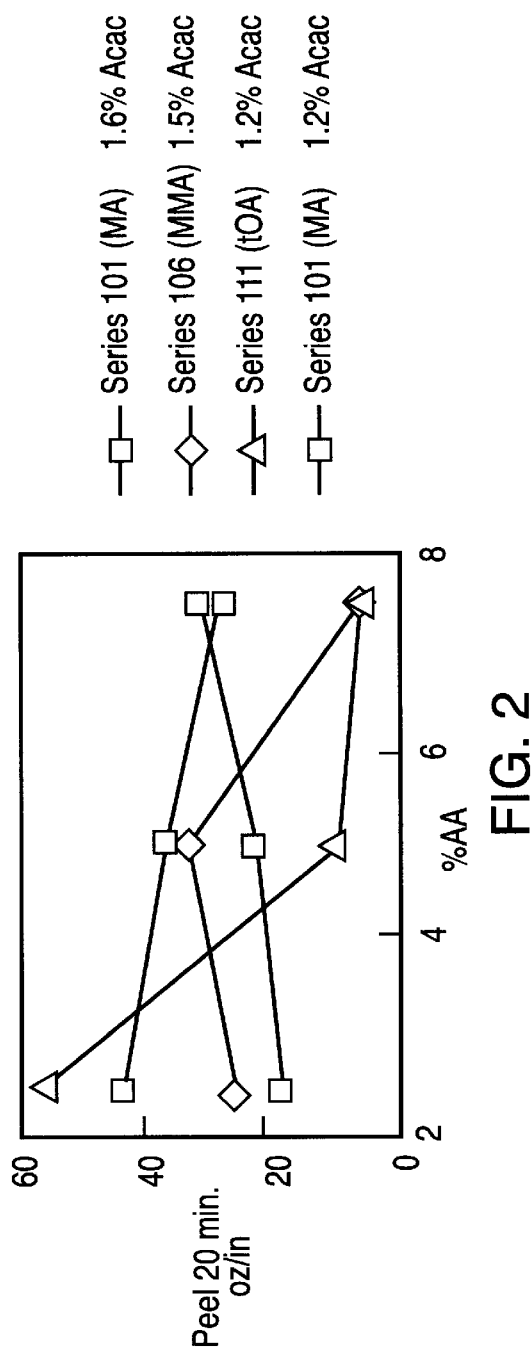

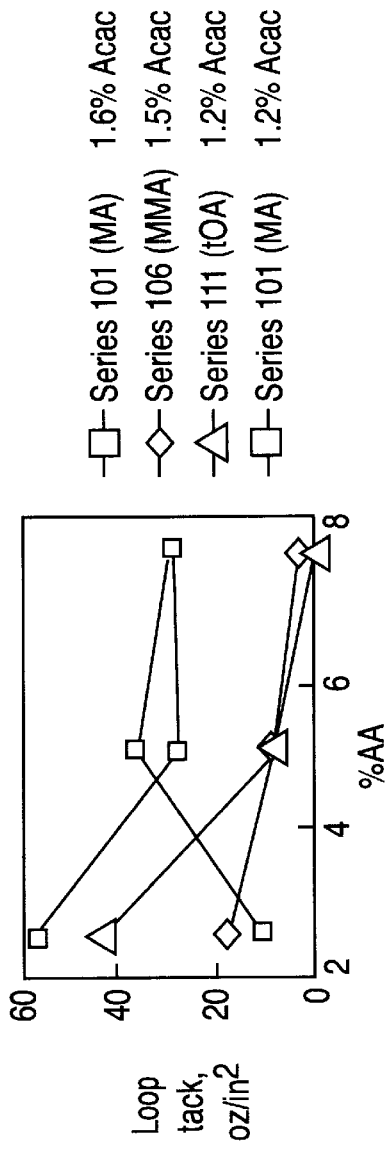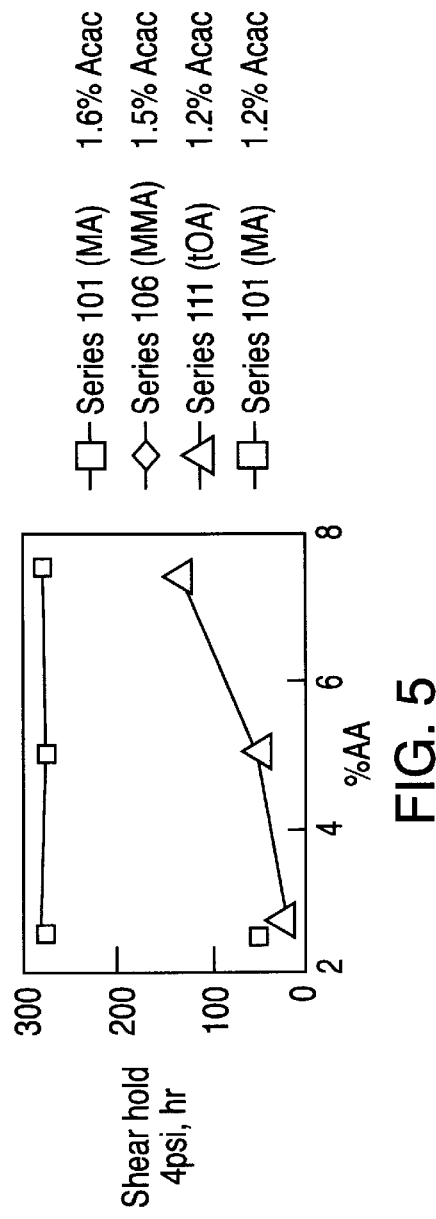

MULTIREACTIVITY POLYMERCAPTANS, STAR POLYMERS AND METHODS OF PREPARATION

BACKGROUND OF THE INVENTION

Star-branched polymers, also known as radial polymers, are characterized by having three or more polymeric arms emanating from a central core. These polymers can be prepared by various polymerization procedures such as anionic, cationic, and free radical mechanisms. The stars are usually formed by using either multifunctional initiators, multifunctional chain transfer agents, or multifunctional coupling agents. The star-branched polymers have unique properties including: narrow molecular weight distributions; low viscosities at low molecular weights or in solution due to their compact structures; high viscosities at high molecular weights due to extensive entanglements.

Heteroarm star polymers have been prepared using free radical methods involving partially capping a polythiol, typically by acetylation, grafting from the uncapped SH groups, removing the blocking group by hydrolysis, and then grafting the second monomer off of the liberated SH groups. U.S. Pat. Nos. 5,399,642 and 5,492,965.

U.S. Pat. No. 5,679,762 discloses the preparation of heteroarm star copolymers by free radical polymerization using sequential addition of monomers. This process relies solely upon the order of addition of monomers for its selectivity.

The present invention improves over the methods of the prior art by using chain transfer agents containing thiol groups with multiple reactivities. Thus, the selectivity is controlled by both the order of addition of the monomers and the composition of the polymercaptan core. Hence, greater control over the blockiness of the heteroarm star results.

SUMMARY OF THE INVENTION

The present invention is directed to multireactivity polymercaptan cores, star-shaped polymers and methods of preparing such polymers. Specifically, the star polymers of the present invention comprise a polyvalent mercaptan core and three or more polymeric arms which extend radially from the core.

The polyvalent mercaptan core comprises three or more thiol groups. In one embodiment at least two of the thiol groups are of different reactivities. Such cores will be referred to as cores of differential reactivity or heterocores.

The polymers of the present invention are prepared by a process which utilizes cores of differential reactivity having three or more SH groups, wherein at least two of the thiol groups have different chain transfer constants. These cores of differential reactivity, act as chain transfer agents in a free radical polymerization process to produce a star polymer.

DESCRIPTION OF THE FIGURES

The above and other features of the invention will be further described in the following detailed specification considered in conjugation with the accompanying drawings in which:

FIG. 1 is a graph of viscosity as a function of percent acrylic acid.

FIG. 2 is a graph of 20 minute peel as a function of percent acrylic acid.

FIG. 4 is a graph of loop tack as a function of percent acrylic acid.

FIG. 5 is a graph of shear hold as a function of percent acrylic acid.

DETAILED DESCRIPTION OF THE INVENTION

Figure 3:
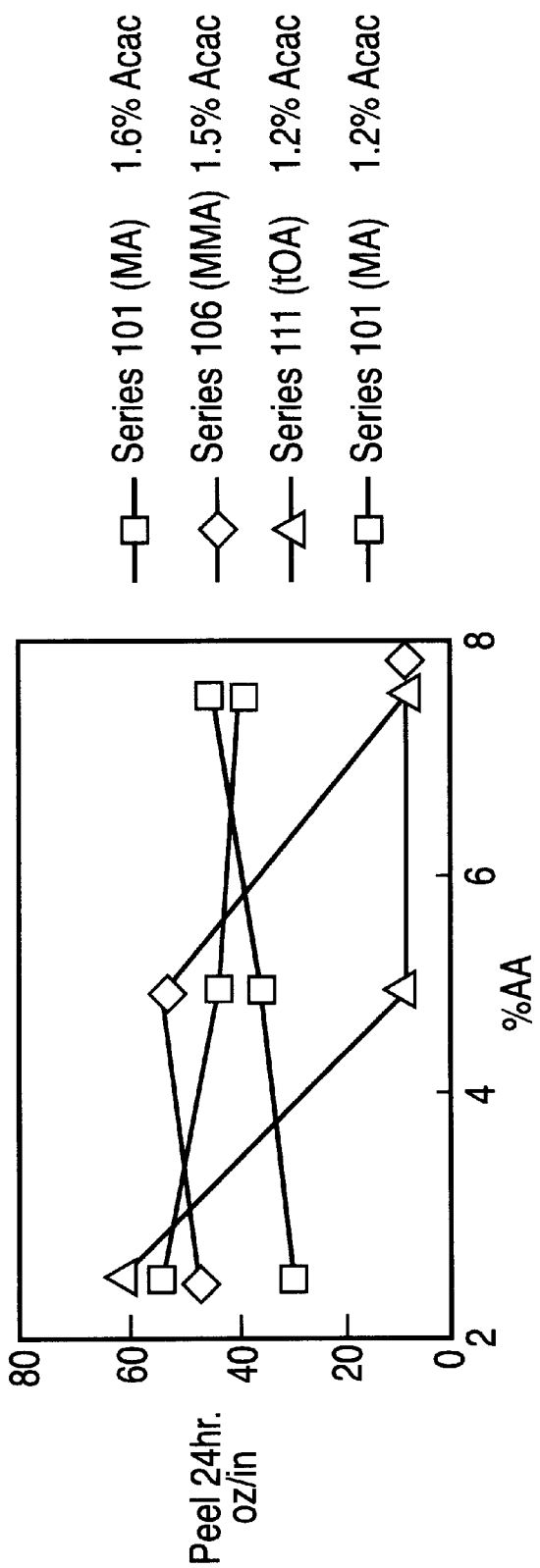
FIG. 3 is a graph of 24 hour peel as a function of percent acrylic acid.

The star polymers of the present invention comprise a polyvalent mercaptan core and three or more polymeric arms which extend radially from the core. The compositions of the arms themselves may be random, blocks or homopolymers.

The polyvalent mercaptan core of the present invention comprises three or more thiol groups, wherein at least two of the thiol groups are of different reactivities, such that the core is of differential reactivity or a heterocore. It is at the thiol groups that the monomers will react to create the polymeric arms of the star polymer. Cores comprising thiol groups, all of which are of the same composition and reactivity will be referred to as homocores.

Specifically, the polyvalent mercaptan core comprises a central component, derived from a multifunctional alcohol which has been substituted with thiol derivatives. The multifunctional alcohol can have any number of functional hydroxy units, preferably 3 to 8 functional units. To prepare the core of the present invention, each of the OH functional units will be substituted with thiol units, preferably at least 2 of which are of different compositions.

In one embodiment of the present invention, the polyvalent mercaptan core is of the general formula:

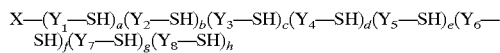

or one of the following specific embodiments:

     (I)

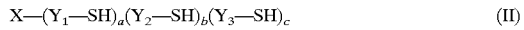     (II)

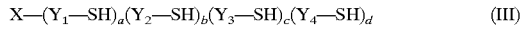     (III)

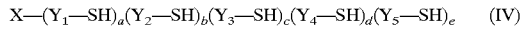     (IV)

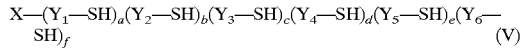     (V)

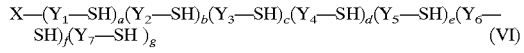     (VI)

or

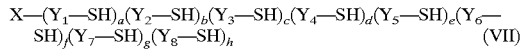     (VII)

wherein X is derived from an organic radical having a valence of 3 to 8. Preferably, X is derived from a tri- to octa-multi-functional alcohol such as glycerol, sorbitol, trimethylolpropane, pentaerythritol, dipentaerythritol, tripentaerythritol, and inositol.

Variables $Y_1$, $Y_2$, $Y_3$, $Y_4$, $Y_5$, $Y_6$, $Y_7$ and $Y_8$ are the same or different and each comprises $C_{2-10}$ alkanoic acids, preferably $C_{2-6}$ alkanoic acids. Variables a and b are integers from 1 to 8 and variables c, d, e, f, g and h are integers from 0 to 8, provided that $a+b+c+d+e+f+g+h \leq 8$.

Each of the above identified (Y—SH) units are derived from, for example, 2-mercaptoacetic acid, 2-mercaptopropionic acid, 3-mercaptopropionic acid, 4-mercaptobutyric acid, 5-mercaptopentanoic acid, or 6-mercaptohexanoic acid. Preferred are 2-mercaptopropionic acid and 3-mercaptopropionic acid.

Examples of cores of differential reactivity within the scope of the present invention include pentaerythritol bis(3-mercaptopropionate) bis(2-mercaptopropionate); trimethylolpropane bis(3-mercaptopropionate)(2-mercaptopropionate); pentaerythritol tris(3-mercaptopropionate)(2-mercaptopropionate); and trimethylolpropane bis (2-mercaptopropionate) (3-mercaptopropionate).

For comparison, cores of non-differential reactivity, or homocores, include pentaerythriol tetrakis(3-mercaptopropionate), trimethylolpropane trithiopropionate, tris(3-mercaptopropionate), pentaerythritol tetrakis (thioglycolate) and dipentaerythritol hexakis(thioglycolate).

In general, the polyvalent mercaptan core is prepared by reacting a multi-functional alcohol with the appropriate amount of mercapto acid to prepare the polyvalent mercaptan core. For example, if the multifunctional alcohol is a tri-alcohol, three equivalents of mercapto acid are added to give three (HS—Y) units. The three equivalents of mercapto acid can be made up of any combination of the preferred mercapto acids. For example, one equivalent of 2-mercaptopropionic acid (a secondary thiol-containing acid) and two equivalents of 3-mercaptopropionic acid (a primary thiol-containing acid) will provide a core of differential reactivity.

In a specific example, pentaerythritol can be used as the multifunctional alcohol, X, used to prepare the core. To pentaerythritol is added 2 mole equivalents each of a primary thiol, 3-mercaptopropionic acid, and a secondary thiol, 2-mercaptopropionic acid. The result will be a mixture of five compounds corresponding to molecules containing ratios of primary/secondary SH groups of 0/4, 1/3, 2/2, 3/1, and 4/0. Those cores with ratios of 1/3, 2/2 and 3/1 are cores of differential reactivity and are within the scope of the present invention. The cores with ratios of 0/4 and 4/0 are homocores. The product mixture, though a statistical mixture, has cores with an average of two primary thiol groups and two secondary thiol groups per core as shown by the following reaction:

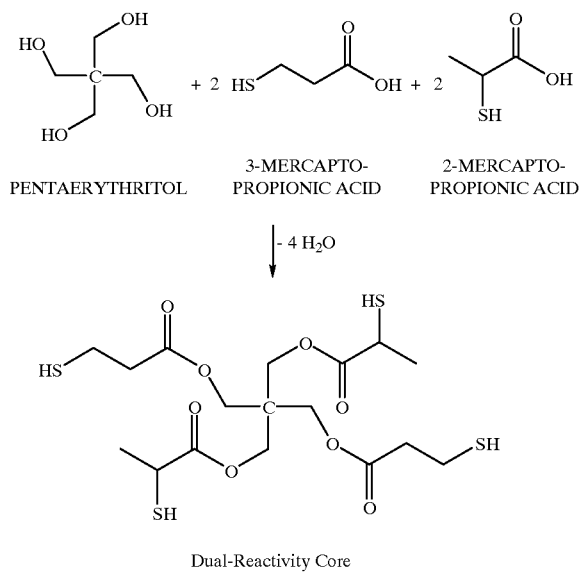

Dual-Reactivity Core

With dipentaerythritol, seven possible compounds can be obtained corresponding to 0,1,2,3,4,5 and 6 primary SH groups per molecule. These differential thiols will be utilized to provide enhanced selectivity to generate heteroarm stars.

For comparison, a homocore can be prepared by adding 4 mole equivalents of thiol to pentaerythritol to prepare a homocore:

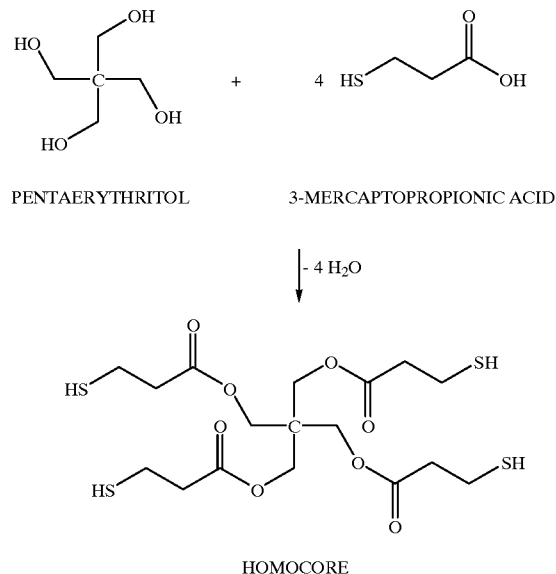

HOMOCORE

The star polymers of the present invention are formed using the mercaptan core as a chain transfer agent in polymerization processes which include bulk, solution, emulsion, and suspension polymerization. Preferably the process is a solution polymerization process employing a free radical initiator. The polymerization reaction is typically conducted at temperatures in the range of 10 to 120° C., preferably 70 to 100° C.

The present invention contemplates that the resulting polymer may comprise arms that are all different, or some different, or all the same after the S atom but with different Y connecting groups.

In one embodiment, the preparation of the star polymers of the present invention is by the non-sequential addition of monomers to a core of differential reactivity. During the process of this embodiment, all of the monomers are added at the same time, i.e., a mixture of two or more monomers are added to the core. The monomers with the higher reactivity ratios in copolymerization will react with the most reactive thiol groups. The polymerization is initiated by a mercapto group on the polyvalent mercaptan core.

In another embodiment, the preparation of the star polymers is by sequential addition of the monomer to the core of differential reactivity. The monomer that is added first will tend to react with the more reactive SH groups. It is preferred that such monomers have a chain transfer constant close to one, i.e., acrylates and methacrylates. The monomers added next will react with the less reactive SH groups. In general, the orders of reactivity of thiol groups are: SH groups attached to aromatic rings (i.e., thiophenols) are more reactive than SH groups attached to primary aliphatic carbon atoms which are more reactive than SH groups attached to secondary aliphatic carbon atoms, i.e., ArSH>RCH$_2$SH>RR'CHSH.

In the process of the above embodiment the polyvalent mercaptan and a first polymerizable unsaturated monomer mixture are radically polymerized. The first monomer mixture could be a single monomer or a mixture of two or more monomers. This polymerization is initiated by a mercapto group on the polyvalent mercaptan core via a standard chain transfer reaction. Because the polyvalent mercaptan group comprises thiol groups of different reactivities, these first monomers will preferably react with the most reactive thiols. The next step comprises the addition of a second polymerizable unsaturated monomer mixture to the product from the first radical polymerization. The second monomer mixture, which may or may not be different from the first unsaturated monomer mixture, is then radically polymerized with the polyvalent mercaptan core. Again because of the different reactivities of the thiol groups on the core, the second monomers will preferably react with the thiol groups of second order of reactivity. This process can be repeated with third, fourth, etc., monomers until all of the thiol groups are reacted. Because of the differences in reactivity of the thiol there is a great deal of control of the blockiness of the final polymer. As used herein, blockiness indicates that the arms of the polymer differ in composition from one arm to the next. The first arms formed are those emanating from the most reactive thiols, the next arms from the next most reactive, etc. Hence greater selectivity, which translates into better control of the blockiness of the polymer, results as compared to the method of U.S. Pat. No. 5,679,762.

In any of the above embodiments, the monomer mixtures can be added by any method familiar to the skilled artisan including dropwise or by slug dose.

Monomers which may be used to prepare the polymeric arms of the star polymers of the present invention include olefinically unsaturated monomers selected from the group consisting of acrylic and methacrylic acids, acrylamide and methacrylamide, acrylonitrile and methacrylonitrile, alkoxyalkyl acrylamides and methacrylamides, e.g., butoxymethyl acrylamide and methoxymethyl methacrylamide, hydroxyalkyl acrylamides and methacrylamides, e.g., N-methylol acrylamide and methacrylamide, the metal salts of acrylic and methacrylic acids, and the esters of acrylic and methacrylic acids with alcohols and phenols; the vinyl aromatic compounds, e.g., styrene, alpha-methylstyrene and substituted derivatives thereof such as the halogenated derivatives thereof and vinyl toluene; the vinyl esters; vinyl amides, e.g., vinyl acetate and vinyl pyrrolidone; ethylencially unsaturated nitriles and combinations thereof.

Monomers may be selected from hydroxyalkyl esters of ethylenically unsaturated carboxylic acids, ethylenically unsaturated carboxylic acids, ethylenically unsaturated epoxides, ethylenically unsaturated isocyanates and combinations thereof.

Other unsaturated monomers include hydroxypropyl (meth)acrylate, glycidyl (meth)acrylate, methoxyethyl (meth)acrylate, ethoxyethyl (meth)acrylate, ethoxyethoxyethyl (meth)acrylate, and the like; vinyl ethers which are represented by methyl vinyl ether, ethyl vinyl ether, isobutyl vinyl ether, and the like; fumaric acid, monoalkyl fumarates, dialkyl fumarates; maleic acid, monoalkyl maleates, dialkyl maleates; itaconic acid, monoalkyl itaconates, dialkyl itaconates; half esters of succinic anhydride or phthalic anhydride with hydroxyethyl (meth)acrylate; (meth)acrylonitrile, butadiene, isoprene, vinyl chloride, vinylidene chloride, vinyl ketones, vinyl pyridine, vinyl carbazole, and the like. These compounds may be used either alone or in combinations with each other.

The present invention also contemplates the use of multifunctional monomers such as ethylene glycol di(meth)acrylate, trimethylolpropane tri(meth)acrylate, diethylene glycol di(meth)acrylate trisacrylate, divinyl benzene, triallyl cyanurate, allyl acrylate, diallyl phthalate, diallyl sucrose.

The preferred monomers are acrylic acid and methacrylic acid and derivatives such as esters and amides which have chain transfer constants with thiols that are close to one. Examples of such monomers are of the formula $CH_2=C(R)COOR'$ where R is H or methyl and R' is H or $C_{1-12}$ alkyl, $C_{5-10}$ cycloalkyl, or $Cr_{6-10}$ aryl wherein the alkyl, cycloalkyl or aryl is optionally substituted with halo or hydroxy. Examples of such monomers include acrylic and methacrylic acid and esters of acrylic acid and methacrylic acid such as methyl acrylate ("MA"), ethyl acrylate ("EA"), n-butyl acrylate ("BA"), 2-ethylhexyl acrylate ("EHA"), 2-hydroxyethyl acrylate, hydroxy propyl acrylate, isobornyl acrylate, methyl methacrylate ("MMA"), ethyl methacrylate, n-propyl methacrylate, isopropyl methacrylate, n-butyl methacrylate, isobutyl methacrylate, cyclohexyl methacrylate, isobornyl methacrylate, 2-ethylhexyl methacrylate, benzyl methacrylate, phenyl methacrylate, hydroxyethyl methacrylate and hydroxypropyl methacrylate ("HPMA").

Methyl methacrylate, 2-ethylhexyl acrylate, methyl acrylate, acrylic acid, butyl methacrylate, 2-hydroxyethyl acrylate and butyl acrylate are the most preferred monomers.

When the polymeric arm is prepared from acrylic and methacrylic monomer units, the polymer arm of the resulting polymer comprises 10 to 1500 monomer units, preferably 20 to 500. When a mixture of monomers is used, the copolymer may be a block or random copolymer of such units. Preferably the copolymer is a random copolymer as produced through conventional free radical polymerization.

Free radical initiators suitable for use in the polymerization process of the present invention include, for example: azo-based polymerization initiators such as 2,2'-azobisisobutyronitrile ("AIBN") and 2,2'-azobis (cyclohexanecarbonitrile); peroxide-based polymerization initiators such as benzoyl peroxide; and the like. Other suitable initiators include organic peroxides, hydroperoxides, persulfates and azo compounds such as methyl ethyl ketone peroxide, cumene hydroperoxide, potassium persulfate, lauroyl peroxide, 2,5-dimethyl-2,5-di (t-butylperoxy)hexane, diethyl peroxide, dipropyl peroxide, dilauryl peroxide, dioleyl peroxide, distearyl peroxide, di(tertiarybutyl) peroxide, di(tertiary amyl) peroxide, tertiary butyl hydroperoxide, tertiary amyl peroxide, acetyl peroxide, propionyl peroxide, lauroyl peroxide, stearoyl peroxide, malonyl peroxide, succinyl peroxide, phthaloyl peroxide, acetyl benzoyl peroxide, propionyl benzoyl peroxide, ascaridole, ammonium persulfate, sodium persulfate, sodium percarbonate, potassium percarbonate, sodium perborate, potassium perborate, sodium perphosphate, potassium perphosphate, tetralin hydroperoxide, tertiary butyl diperphthalate, tertiary butyl perbenzoate, 2,4-dichlorobenzoyl peroxide, urea peroxide, caprylyl peroxide, p-chlorobenzoyl peroxide, 2,2-bis (tertiary butyl peroxy)butane, hydroxyheptyl peroxide.

Whether or not the reaction will require a solvent will depend on the monomers and core selected. If the polymerization process is one which requires a solvent, as determined by one of skill in the art, a solvent can be selected from the group consisting of organic solvents which are represented by: aromatic hydrocarbons such as toluene and xylene; esters such as ethyl acetate and butyl acetate; cycloaliphatic hydrocarbons such as cyclohexane; aliphatic hydrocarbons such as hexane and pentane; ketones such as acetone, methyl ethyl ketone, and methyl isobutyl ketone; aliphatic esters; alcohols; and the like. Other suitable solvents include naphthalene, trichlorobenzene, dimethylformamide and dimethylacetamide.

The following examples are illustrative only and are not intended to limit the scope of the present invention in any manner.

EXAMPLES

The following test procedures were used in the examples:

Solution viscosities were determined on a Brookfield Model RVT viscometer operated at 25 rpm and 22° C.

The peel strength was measured from stainless steel panels in accordance with the Pressure Sensitive Tape Council ("PSTC"), Chicago, Illinois Test Method No. 1. Here, "initial" peel represents a bonded time lapse of 20 minutes rather than the specified 1 minute. "24 hrs OP" indicates a bonded time lapse of 24 hours and is indicative of the tendency for peel strength to increase with time after bonding. The test strip backing is 0.002 inch thick PET (polyethylene terephthalate) film and the dry adhesive coating weight is 25 g/m$^2$. The dry adhesive coatings are preconditioned overnight and then tested at 22° C. and 50% R.H. The average test results are recorded in units of ounces per inch width.

The shear test is conducted in accordance with PSTC Test Method No. 7. The coating preparation, preconditioning and test conditions are the same as for the peel test. Fifteen minutes elapsed time after bonding is allowed before attaching the load. A 1 kg weight is used on 1 square inch of bonded area giving 4.4 psi (nominally indicated as 4 psi in the Tables). The average time to failure is recorded in hours.

Dynamic Mechanical Analysis: The temperature spectrum of linear viscoelastic properties for the dry adhesive film is determined at 10 radians/second over the range from −70° to +190° C. using a Rheometrics Model RDA700 rheometer.

Example I

Preparation of an Octa-Functional Core of Differential Reactivity

An octa-functional polymercaptan core with differential reactivity in accordance with the present invention was prepared in the following manner. To a one liter flask was added 75.00 grams of tripentaerythritol (0.2 mol; 1.6 moles hydroxy groups), 94.29 grams of 2-mercaptopropionic acid (0.89 mol, 0.55 equivalents), 94.29 grams of 3-mercaptopropionic acid (0.89 mol, 0.55 equivalents) and 300 grams of toluene. A catalyst solution prepared from 0.75 grams of p-toluenesulfonic acid in 1 ml of water was added in a single shot. The mixture was stirred and heated to reflux, 115° C. The reaction was driven by azeotropic removal of water using a Dean-Stark apparatus. Heating was discontinued once the theoretical amount of water had been removed. In this case, 29 ml of water was collected. After the reaction is complete, excess mercapto acid was neutralized with NaHCO$_3$. The solvent was then removed under vacuum to yield the multi-reactivity polymercaptan core.

Example II

Preparation of a Tetra-Functional Core of Differential Reactivity

A tetra-functional polymercaptan core with differential reactivity in accordance with the present invention was prepared in the following manner. To a two liter flask was added 68.1 grams of pentaerythritol (0.5 mol, 2 moles 30 hydroxy groups), 116.8 grams of 2-mercaptopropionic acid (1.1 mol, 0.55 equivalents), 116.8 grams of 3-mercaptopropionic acid (1.1 mol, 0.55 equivalents) and 250 grams of toluene. A catalyst solution prepared from 1.5 grams of p-toluene sulfonic acid in 2 ml of water was added in a single shot. The mixture was stirred and heated to reflux, 115° C. The reaction was driven by azeotropic removal of water using a Dean-Stark apparatus. Heating was discontinued once the theoretical amount of water had been removed. In this case, 38 ml of water was collected. After the reaction was complete, excess mercapto acid was neutralized with sodium bicarbonate. The solvent was then removed under vacuum to yield the multi-reactivity polymercaptan core.

The results of $^{13}$C NMR shows 5 peaks for the quaternary carbon of the pentaerythritol esters at chemical shift 42 ppm, which indicates a perfect statistical distribution of the expected five products from the reaction of pentaerythritol with 2 moles of 3-mercaptopropionic acid and 2 moles of 2-mercaptopropionic acid (i.e. 0:4,1:3,2:2,3:1,4:0).

Example III

Preparation of 4-Armed Star Polymer from a Tetra-Functional Core of Differential Reactivity A star polymer in accordance with the present invention was prepared in the following manner. Butyl methacrylate, 25 grams, and 6.5 grams bis(3-mercaptopropionate) bis(2-mercaptopropionate) pentaerythritol, prepared according to Example II, were added to 200 grams ethanol, stirred and heated to reflux, approximately 80° C. To the mixture, half of an initiator solution (1.0 g azobisisobutyronitrile [AIBN] in 10 ml ethanol) was added. After approximately 90 minutes the heat was removed and 25 grams butyl acrylate and 150 grams acrylic acid along with the second half of the initiator solution were added. The mixture was stirred and heated for an additional two hours. To the mixture was added a sodium hydroxide solution prepared from 20 grams of sodium hydroxide in 200 ml of water. Following addition of the sodium hydroxide solution, more water is added to give a final mixture of 10% solids. The result is a clear solution of a heteroarm star polymer with a theoretical molecular weight of 15,000. The clarity of the solution is indicative of the absence of butyl methacrylate homopolymer and, thus, the formation of heteroarm polymer whereupon each star has arms of both butyl methacrylate and butyl acrylate-co-sodium acrylate. The solution was freeze dried to yield a white powder.

Example IV

Preparation of 4-Armed Star Polymer from a Homocore

For comparison, a star polymer was prepared from a non-multiple reactivity core in the following manner: Butyl methacrylate, 25 grams, and 6.5 grams pentaerythritol tetrakis(3-mercaptopropionate) were added to 200 grams ethanol, stirred and heated to reflux, approximately 80° C. To the mixture, half of an initiator solution (1.0 g azobisisobutyronitrile [AIBN] in 10 ml ethanol) was added. After approximately 90 minutes the heat was removed and 25 grams butyl acrylate and 150 grams acrylic acid along with the second half of the initiator solution were added. The mixture was stirred and heated for an additional two hours. To the mixture was added a sodium hydroxide solution prepared from 20 grams of sodium hydroxide in 200 mls of water. Following addition of the sodium hydroxide solution, more water is added to give a final mixture of 10% solids. The result was a slightly turbid solution/suspension of a heteroarm star polymer with a theoretical molecular weight of 15,000. The very slight turbidity observed may indicate the presence of some butyl methacrylate homopolymer which is insoluble in water.

To avoid the formation of a turbid solution, the above process was repeated but with very careful control of the level of conversion with butyl methacrylate, before addition of the butyl acrylate/acrylic acid. In the above reaction sequence, when the first polymerization step was allowed to proceed only 70 minutes, instead of 90 minutes, a clear solution was obtained.

However, for star formation utilizing the multi-reactivity core (as in Example III) control of the processing parameters, such as the time allowed for conversion of the first monomer, are not so critical. This is because, on average, the multiple thiol cores have two thiol terminated arms that are relatively unreactive (secondary thiol) and two thiol terminated arms that are relatively reactive (primary thiol). The less reactive thiols will tend only to react when the second step monomer is added and the reaction allowed to proceed for the two hours. This ensures that all stars formed will contain both monomers in a blocky form.

Example V

A mixture of acrylates in the ratio of 70 parts 2-ethylhexyl acrylate, 27.5 parts t-octyl acrylamide and 2.5 parts acrylic acid were polymerized in the presence of 0.65 parts tetrafunctional polymercaptan pentaerythritol bis(2-mercaptopropionate)bis(3-mercaptopropionate) to yield a star polymer, Sample 5-A. For comparison, the same monomer composition was polymerized in the presence of linear methyl 3-mercaptopropionate to prepare a linear control, Sample 5-B. The reagents and procedure for preparation of each sample were as described below.

| Materials | Weight (g) |
|---|---|
| Monomer Mix: | |
| 2-Ethylhexyl acrylate | 700 |
| t-octyl acrylamide | 275 |
| Acrylic acid | 25 |
| Polymercaptan | 6.5 |
| Initial Charge: | |
| Monomer mix | 335.5 |
| Ethyl acetate | 217 |
| Monomer Slow Add: | |
| Monomer mix | 671 |
| Initiator Slow Add: | |
| Ethyl acetate | 60 |
| 2,2'-Azobisisobutyronitrile | 5 |
| Total Weight | 1288.5 |
| Theoretical Solids | 78.5 |

The monomer mix was prepared and thoroughly mixed. The initial charge was charged to a 3000 mL reaction flask, equipped with a condenser, paddle stirrer, thermometer, addition funnels and water bath. The initial charge was heated to reflux and held for 5 minutes. At reflux, add very slowly 50% by volume of initiator solution to the flask contents. After 10 minutes hold, monomer and initiator were slow added continuously and uniformly over 3 hours while maintaining reflux. At the end of slow adds, the flask contents were held at reflux for 2 hours. The contents were then cooled to 25° C. and analyzed for residual monomers, % solid, intrinsic viscosity and molecular weight, and the data shown below in Table I. TYZOR GBA is a chelated titanium ester from DuPont.

TABLE 1

| Sample | 5-A | 5-B |
|---|---|---|
| Type of Polymer | Heterocore | Linear |
| B.F. Visc. @ 24° C. | 35,000 cps | 103,000 cps |
| Solids (%) | 77.45 | 77.66 |
| Coating thickness | 1.5 mil | 1.5 mil |
| Substrate | 2 mil PET | 2 mil PET |
| TYZOR GBA | 2% | 2% |
| Peel, initial, 20 min @ RT (oz/in) | 55 | 42 |
| Peel, 24 hrs OP @ RT (oz/in) | 84 | 59 |
| Shear, 4 PSI @ RT (hr) | 4.5 | 40 |

Example VI

Stage I: Preparation of base polymer:

A mixture of acrylates in the ratio of 50 parts 2-ethylhexyl acrylate, 35 parts methyl acrylate and 10 parts butyl acrylate were polymerized with 5 parts hydroxypropyl methacrylate in the presence of different levels of (0.25, 0.5, 0.75 parts) pentaerythritol tetrakis(3-mercaptopropionate) as a chain transfer agent to give a polymer with 0.35 mmol hydroxy functionality per gram of polymer. The reagents and procedure were as described below for 0.25 parts pentaerythriol tetrakis(3-mercaptopropionate).

| Materials | Weight (g) |
|---|---|
| Monomer Mix: | |
| 2-Ethylhexyl acrylate | 250 |
| Methyl acrylate | 175 |
| Butyl acrytate | 50 |
| Hydroxypropyl methacrylate | 25 |
| Pentaerythritol tetrakis(3-mercaptopropionate) | 1.25 |
| Initial Charge: | |
| Monomer mix | 50 |
| Ethyl acetate | 80 |
| 2,2'-Azo-bis(2-methylbutanenitrile) | 0.5 |
| Monomer Slow Add: | |
| Monomer mix | 450 |
| Initiator Slow Add: | |
| Ethyl acetate | 60 |
| 2,2'-Azo-bis(2-methylbutanenitrile) | 5 |

The monomer mix was prepared and thoroughly mixed. The initial charge was charged to a 1000 mL reaction flask, equipped with a condenser, paddle stirrer, thermometer, addition funnels and water bath. The initial charge was heated to reflux and held for 10 minutes. Monomer mix and initiator solution were slow added simultaneously and continuously over 2 and 3 hours respectively while maintaining reflux. At the end of initiator slow add, reaction mixture was held at reflux for 3 hours. The contents were cooled to 25° C. and analyzed for residual 2-ethylhexyl acrylate ("2-EHA"), butyl acrylate ("BA"), methylacrylate ("MA"), hydroxypropyl methacrylate ("HPMA"), percent solid, intrinsic viscosity and molecular weight. The base polymer prepared with 0.25 parts pentaerythriol tetrakis(3-mercaptopropionate) is designated Base Polymer 1A; with 0.5 parts, Base Polymer 1B; with 0.75 parts, Base Polymer 1C.

Stage-II: Urethane reaction and solvent strip:

The reaction was carried out in the same flask with the same set-up with the addition of a $CaCl_2$ drying tube on top of the condenser. The olefinic monomer 1-(1-isocyanato-1-methyl ethyl)-3-(1-methyl ethenyl)benzene ("m-TMI") 0.14 mmol/g of polymer was added to the base polymer solutions (1A, 1B, 1C) and stirred for 10 minutes at 30° C. Dibutyltin dilaurate catalyst $4.38 \times 10^{-4}$ g/g of polymer was added to the reaction mixture. The reaction mixture was stirred for an additional 10 minutes and heated to reflux for 12 hours. When the reaction was complete, the solvent was stripped under reduced pressure (10–30 mm Hg) at 95° C. and the reaction product was discharged while still at approximately 80° to 90° C.

UV cure polymer:

Samples for UV curing polymers were prepared by adding 2% IRGACURE 184 (1-hydroxycyclohexyl phenyl ketone) photoinitiator after the completion of the reaction and before vacuum stripping the solvent.

Analytical properties for base polymers are listed in the following table:

TABLE 2

| BASE POLYMER: | 1A | 1B |
|---|---|---|
| Pentaerythritol tetrakis (3-mercaptopropionate) (parts) | 0.25 | 0.5 |
| % Solid | 75.99 | 75.75 |
| Mw | 137,000 | 101,000 |
| Mn | 24,600 | 18,200 |
| Sample | 1A-1 | 1B-1 |
| Base polymer | 1A | 1B |
| Curing radiation | EB | EB |

| SAMPLE | 1A-1 | 1B-1 | Control |
|---|---|---|---|
| Polymer | 4-arm star | 4-arm star | linear |
| viscosity @ 300° F. | 30,000 cps | 15,000 cps | 10,000 cps |
| Coating thickness | 1 mil | 1 mil | 1 mil |
| substrate | 2 mil PET | 2 mil PET | 2 mil PET |
| dosage | 6 Mrads | 6 Mrads | 6 Mrads |
| Accelerating Voltage | 165 kV | 165 kV | 165 kV |
| Peel, initial, 20 min @ RT (oz/in) | 28 | 30 | 29.5 |
| Peel, 24 hrs OP @ RT (oz/in) | 30 | 43 | 35.5 |
| Shear 4 PSI @ RT(hr) | 91 | 37.5 | 27 |

Example VII

A mixture of acrylates in the ratio of 50 parts 2-ethylhexyl acrylate, 35 parts methyl acrylate and 10 parts butyl acrylate were polymerized with 5 parts hydroxypropyl methacrylate in the presence of different levels of (0.25 and 0.5 parts) tetrafunctional polymercaptan, pentaerythritol bis(2-mercaptopropionate) bis(3-mercaptopropionate) to give a polymer with 0.35 mmol hydroxy functionality per gram of polymer, base polymers 6A and 6B. For comparison purpose, polymers were prepared by equimolar replacement of tetrafunctional polymercaptan with linear methyl 3-mercaptopropionate, and polymers without any chain transfer agent were prepared, samples 6C, 6D, 6E. The procedure used for base polymer preparation and urethane reaction was same as listed for Example VI. Samples 6A, 6C, 6B, 6D, 6E were functionalized with m-TMI and designated 6A-1, 6C-1, 6B-1, 6D-1, 6E-1, respectively. Solvent was not removed, and the samples analyzed in a solution form. The results are shown below in Table 3. Samples 6A-1 and 6C-1 where cured at different energy levels, and the results shown in Table 4.

The results in Tables 3 and 4, indicate that star polymers, when compared to linear polymer prepared with equivalent amounts of chain transfer agent, had lower solution viscosity. See for examples the results for samples 6A vs. 6C and 6B-1 vs. 6D-1.

Both 6A and 6B, which are 4-arm star polymer, and the linear control polymer are not functionalized with pendant C=C. Samples 6A-1 and 6B-1 are functionalized versions of 6A and 6B respectively. The results in the table indicate that polymer with C=C functionality efficiently crosslinks with radiation giving high cohesion. Furthermore, star polymer 6A-1, which has a lower apparent molecular weight, has better adhesive properties than the linear version of the same polymer. Similarly, star polymer 6A-1 has better pressure sensitive properties, peel adhesion and tack, than linear polymer 6C-1 which has the highest molecular weight among the series tested. These results demonstrate the advantage of a star polymer with pendant C=C functionality in radiation curable pressure sensitive adhesives.

TABLE 3

| Sample | 6A Comparative | 6C Comparative | 6A-1 | 6C-1 | 6B-1 | 6D-1 | 6E-1 |
|---|---|---|---|---|---|---|---|
| Mercaptan | Heterocore | Linear | Heterocore | Linear | Heterocore | linear | none |
| B.F. Visc. @ 24° C. | 45,000 cps | 130,000 cps | 45,400 cps | 141,000 cps | 14,000 cps | 64,000 cps | 119,000 cps |
| Solids (%) | 74.64 | 75.37 | 72.65 | 73.28 | 73.32 | 73.07 | 73.29 |
| Coating thickness | 1.5 mil | 1.5 mil | 1.5 mil | 1.5 mil | 1.5 mil | 1.5 mil | 1.5 mil |
| Substrate | 2 mil PET | 2 mil PET | 2 mil PET | 2 mil PET | 2 mil PET | 2 mil PET | 2 mil PET |
| Dosage | 6 Mrads | 6 Mrads | 6 Mrads | 6 Mrads | 6 Mrads | 6 Mrads | 6 Mrads |
| Kv | 165 Kv | 165 Kv | 165 Kv | 165 Kv | 165 Kv | 165 Kv | 165 Kv |
| Peel, initial, @ RT (oz/in) | 89.5 | 135.5 | 31.5 | 34.5 | 30.5 | 20.5 | 22 |
| Peel, 24 hrs OP @ RT (oz/in) | 95.5 | 130.5 | 35.5 | 33 | 46 | 25 | 30.5 |
| Shear, 4 PSI @ RT (hr) | 3 min | 23 min | 29.3 | 15.4 | 14.3 | 25.4 | 27.7 |
| Mw | 136,000 | 197,000 | 136,000 | 197,000 | 85,200 | 168,000 | 224,000 |
| Mn | 21,500 | 22,500 | 21,500 | 22,500 | 17,900 | 23,900 | 26,200 |

TABLE 4

| Sample | 6A-1 | 6C-1 | 6A-1 | 6C-1 | 6A-1 | 6C-1 |
|---|---|---|---|---|---|---|
| Mercaptan | Heterocore | Linear | Heterocore | Linear | Heterocore | Linear |
| B.F. Visc. @ 24° C. | 45,400 | 141,000 | 45,400 | 141,000 | 45,400 | 141,000 |
| Solids (%) | 72.65 | 73.28 | 72.65 | 73.28 | 72.65 | 73.28 |
| Coating thickness | 1.5 mil | 1.5 mil | 1.5 mil | 1.5 mil | 1.5 mil | 1.5 mil |
| Substrate | 2 mil PET | 2 mil PET | 2 mil PET | 2 mil PET | 2 mil PET | 2 mil PET |
| Energy Level | 0.95 J/cm2 | 0.95 J/cm2 | 1.41 J/cm2 | 1.41 J/cm2 | 2.19 J/cm2 | 2.19 J/cm2 |
| UV Source | 1 D bulb | 1 D bulb | 1 D bulb | 1 D bulb | 1 D bulb | 1 D bulb |
| Peel, initial, @ RT (oz/in) | 96 | 51 | 92 | 42 | 87 | 37 |
| Peel, 24 hrs OP @ RT (oz/in) | 82.5 | 63 | 104 | 51.5 | 102 | 41 |
| Shear, 4 PSI @ RT (hr) | 7 min | 95 min | 7 min | 100 min | 13 min | >250 hrs |
| Mw | 136,000 | 197,000 | 136,000 | 197,000 | 136,000 | 197,000 |
| Mn | 21,500 | 22,500 | 21,500 | 22,500 | 21,500 | 22,500 |

Example VIII

A mixture of acrylates in the ratio of 50 parts 2-ethylhexyl acrylate, 35 parts methyl acrylate and 10 parts butyl acrylate were polymerized with 5 parts hydroxypropyl methacrylate in the presence of different levels of (0.25 and 0.5 parts) tetrafunctional polymercaptan with dual reactivity, pentaerythritol bis(2-mercaptopropionate) bis(3-mercaptopropionate), to give a polymer with 0.35 mmol hydroxy functionality per gram of polymer. Samples 7A and 7B, respectively. The procedure used to make the polymer, by sequential addition of monomers, is described below.

Ethyl acetate, 2-EHA, HPMA and VAZO 67, an azo initiator available from DuPont were charged as an initial charge to the flask and heated to reflux. After 10 minutes of the reflux, started monomer slow add-1 containing 2-EHA, HPMA and polymercaptan over 1 hour. Simultaneously initiator slow add-3 containing ethyl acetate ("EtOAc") and VAZO 67 started over 4h. At the end of monomer slow add-1, wait for 1 hour. Started monomer slow add-2 over 2 hour. At the end of slow adds, hold for 2 hour. The contents were cooled to 25° C. and analyzed for residual 2-EHA, BA, MA, HPMA, percent solid, intrinsic viscosity and molecular weight.

Procedure used for urethane reaction was same as mentioned in Example VI. Final polymers were E-Beam cured and analyzed in solution form and the results shown below in Table 5.

TABLE 5

EBEAM CURABLE STAR BRANCHED POLYMERS

| Sample ID | 7A | 7B |
|---|---|---|
| Mercaptan | Heterocore | Heterocore |
| B.F. Visc. @ 24 C. | 124,000 cps | 70,000 cps |
| Solids (%) | 77.4 | 77.3 |
| Coating thickness | 1.5 mil. | 1.5 mil. |
| Substrate | 2 mil PET | 2 mil PET |
| Dosage | 6 Mrads | 6 Mrads |
| Kv | 165 Kv | 165 Kv |
| Peel, initial 20 min. @ RT (oz/in) | 5.5 | 19.5 |
| Peel,24hrs OP @ RT (oz/in) | 10 | 30.5 |
| Shear, 4 PSI @ RT(hr) | 10.4 hrs | 2.3 hrs |
| Iv | 0.339 | 0.268 |
| Mw | 95,600 | 73,900 |
| Mn | 20,900 | 17,900 |
| D | 4.57 | 4.13 |

Example IX

A mixture of acrylates in the ratio of 70 parts 2-ethylhexyl acrylate, 27.5 parts t-octyl acrylamide and 2.5 parts acrylic acid were polymerized in the presence of 0.65 parts tetrafunctional polymercaptan pentaerythritol bis(2-mercaptopropionate) bis(3-mercaptopropionate), to yield a heterocore star polymer. For comparison, the same monomer composition was polymerized in the presence of equimolarly substituted linear methyl 3-mercaptopropionate to provide a linear control polymer. The reagents and procedure for preparation of each sample were as described below.

| Materials | Weight (g) |
|---|---|
| Monomer Mix: | |
| 2-Ethylhexyl acrylate | 700 |
| t-Octyl acrylamide | 275 |
| Acrylic acid | 25 |
| Polymercaptan | 6.5 |
| Initial Charge: | |
| Monomer mix | 335.5 |
| Ethyl acetate | 217 |
| Monomer Slow Add: | |
| Monomer mix | 671 |
| Initiator Slow Add: | |
| Ethyl acetate | 60 |
| 2,2'-Azobisisobutyronitrile | 5 |
| Tota Weight | 1288.5 |
| Theoretical Solids | 78.5 |

The monomer mix was prepared and thoroughly mixed. The initial charge was charged to a 3000 mL reaction flask, equipped with a condenser, paddle stirrer, thermometer, addition funnels and water bath. The initial charge was heated to reflux and held for five minutes. At reflux, very slowly add 50% by volume of initiator solution to the flask contents. After 10 minutes hold, monomer and initiator were slow added continuously and uniformly over three hours while maintaining reflux. At the end of slow adds, the flask contents were held at reflux for two hours. The contents were cooled to 25° C. and analyzed for residual monomers, percent solid, intrinsic viscosity and molecular weight, and the results shown below.

TABLE 6

| Sample | 9-A | 9-B |
| --- | --- | --- |
| Type of Polymer | Heterocore | Linear |
| B.F. Visc. @ 24° C. | 35,000 cps | 103,000 cps |
| Solids (%) | 77.45 | 77.66 |
| Coating thickness | 1.5 mil | 1.5 mil |
| Substrate | 2 mil PET | 2 mil PET |
| TYZOR GBA | 2% | 2% |
| Peel, initial, 20 min @ RT (oz/in) | 55 | 42 |
| Peel, 24 hrs OP @ RT (oz/in) | 84 | 59 |
| Shear, 4 PSI @ RT (hr) | 4.5 | 40 |

Example X

A mixture of acrylates in the ratio of 70 parts 2-ethylhexyl acrylate, 27.5 parts t-octyl acrylamide and 2.5 parts acrylic acid were polymerized in the presence of 0.65 parts tetrafunctional polymercaptan, pentaerythritol tetrakis(3-mercaptopropionate) to yield a star polymer. The reagents and procedure for preparation of each sample were as described below.

| Materials | Weight (g) |
| --- | --- |
| Monomer Mix: | |
| 2-Ethylhexyl acrylate | 70 |
| t-Octyl acrylamide | 27.5 |
| Acrylic acid | 2.5 |
| Polymercaptan | 0.65 |
| Initial Charge: | |
| Monomer mix | 33.3 |

| Materials | Weight (g) |
| --- | --- |
| Ethyl acetate | 21.7 |
| Monomer Slow Add: | |
| Monomer mix | 45 |
| Initiator Slow Add: | |
| Ethyl acetate | 6.0 |
| 2,2′-Azobisisobutyronitrile | 0.5 |

The monomer mix was prepared and thoroughly mixed. The initial charge was charged to a 3000 mL reaction flask, equipped with a condenser, paddle stirrer, thermometer, addition funnels and water bath. The initial charge was heated to reflux and held for 5 minutes. At reflux, add very slowly 50% by volume of initiator solution to the flask contents. After 10 minutes hold, monomer and initiator were slow added continuously and uniformly over three hours while maintaining reflux. At the end of slow adds, the flask contents were held at reflux for two hours. The contents were cooled to 25° C. and analyzed, and the results shown below. Other monomers and reagents were also prepared by the above method and these results also shown in Table 7 below.

TABLE 7

| | 101A | 101B | 101C | 106A | 106B | 106C | 111A | 111B | 111C | 101C | 106C | 111C |
| --- | --- | --- | --- | --- | --- | --- | --- | --- | --- | --- | --- | --- |
| 2-EHA | 65 | 65 | 65 | 65 | 67.5 | 70 | 65 | 67.5 | 70 | 65 | 70 | 70 |
| MA methylmethacrylate, MMA | 27.5 | 30 | 32.5 | 27.5 | 27.5 | 27.5 | | | | 32.5 | 27.5 | |
| tOA | | | | | | | 27.5 | 27.5 | 27.5 | | | 27.5 |
| AA | 7.5 | 5 | 2.5 | 7.5 | 5 | 2.5 | 7.5 | 5 | 2.5 | 2.5 | 2.5 | 2.5 |
| polymercaptan | 0.65 | 0.65 | 0.65 | 0.65 | 0.65 | 0.65 | 0.65 | 0.65 | 0.65 | 0.65 | 0.65 | 0.65 |
| Final Solids (%) | 50 | 50 | 50 | 50 | 50 | 50 | 50 | 50 | 50 | 50 | 50 | 50 |
| Final Viscosity (%) | 425 | 350 | 275 | 525 | 362 | 250 | 425 | 275 | 225 | 275 | 250 | 225 |
| AlAcAc/2,4PD/Toluene* | 1.6% | 1.6% | 1.6% | 1.6% | 1.6% | 1.6% | 1.2% | 1.2% | 1.2% | 1.2% | 1.2% | 1.4% |
| Coat Wt (lbs/ream) | 17.2 | 17.4 | 16.1 | 17.9 | 17.5 | 16.4 | 16.1 | 17.1 | 16.2 | 16.4 | 16.4 | 17.2 |
| Peel, 20 min, @ RT (oz/in) avg | 30.5 | 22.5 | 17 | 6 | 33 | 24.5 | 5.5 | 9.5 | 57 | 28.5 | 37 | 43.5 |
| Peel, 24 hrs OP @ RT (oz/in) avg | 44.5 | 36 | 29 | 6 | 52 | 45 | 4 | 10.5 | 60.5 | 39.5 | 43.5 | 53 |
| Shear, 4 PSI (hr) avg | 280 | 280 | 280 | 280 | 280 | 280 | 136.5 | 53.8 | 23.1 | >50 | >50 | 51.9 |
| Loop Tack (oz/in²) avg | 30 | 36 | 10 | 4 | 8.5 | 17.5 | 0 | 8 | 43 | 29.5 | 28 | 57 |

*AlAcAc = aluminum acetylacetonate
2,4PD = 2,4 pentanedione

Viscosity, peel, shear and loop tack were plotted against percent acrylic acid, and the results shown in FIGS. 1–5. FIG. 1 indicates that tOA gives the lowest viscosity and that in general, viscosity increases with an increase in acrylic acid content. FIG. 2 shows 20 minute peel as a function of acrylic acid content. In general, peel decreases with increase in acrylic acid content, although sometimes a maximum is seen such as with the 106 series containing methyl methacrylate. The steepest decline in peel is seen in the 111 series which contains tOA. However in all cases, peel values are in the range of 20 to 60 oz/inch. FIG. 3 shows 24 hour peel, and the tends are exactly the same as in FIG. 2, however the peel values are all higher indicating a build up with time. FIG. 4 shows loop tack values for all the samples. FIG. 5 shows the shear holds for the same polymer.

We claim:

1. A mercaptan core of differential reactivity of the general formula:

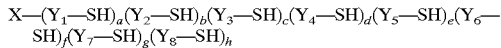

wherein X is derived from an organic radical having a valence of 3 to 8; $Y_1$, $Y_2$, $Y_3$, $Y_4$, $Y_5$, $Y_6$, $Y_7$ and $Y_8$ are the same or different from each other but are not all the same and each comprise $C_{2-10}$ alkanoic acid; a and b are integers from 1 to 8, and c, d, e, f, g, h are integers from 0 to 8 provided that $a+b+c+d+e+f+g+h \leq 8$.

2. A mercaptan core according to claim 1 wherein X is the residue of a tri- to -octa functional alcohol.

3. A mercaptan core according to claim 1 wherein X is a residue of glycerol, sorbitol, trimethylolpropane, pentaerythritol, dipentaerythritol, tripentaerythritol, and inositol.

4. A star shaped polymer comprising:
   a) a mercaptan core according to claim 1; and
   b) two or more polymer segments which extend radially from the mercaptan core.

5. A star shaped polymer according to claim 4 wherein X is the residue of a tri- to -octa functional alcohol.

6. A star shaped polymer according to claim 4 wherein X is a residue of glycerol, sorbitol, trimethylolpropane, pentaerythritol, dipentaerythritol, tripentaerythritol, and inositol.

7. A star shaped polymer according to claim 4 wherein the polymer segments comprise monomers selected from the group consisting of the esters and amides of acrylic and methacrylic acids with alcohols, phenols and amines; the vinyl aromatic compounds, and substituted derivatives thereof; vinyl esters; vinyl amides, ethylenically unsaturated nitriles, hydroxyalkyl esters of ethylenically unsaturated carboxylic acids, ethylenically unsaturated carboxylic acids, ethylenically unsaturated epoxides, ethylenically unsaturated isocyanates, ethylene glycol di(meth)acrylate, trimethylolpropane tri(meth)acrylate, diethylene glycol di(meth)acrylate, divinyl benzene, triallyl cyanurate, allyl acrylate, diallyl phthalate, diallyl sucrose and combinations thereof.

8. A process for preparing a star polymer comprising polymerizing a mercaptan core according to claim 1 and one or more compatible monomers.

9. The process of claim 8 wherein the monomers are selected from the group consisting of monomers selected from the group consisting of the esters and amides of acrylic and methacrylic acids with alcohols, phenols and amines; the vinyl aromatic compounds, and substituted derivatives thereof; vinyl esters; vinyl amides, ethylenically unsaturated nitriles, hydroxyalkyl esters of ethylenically unsaturated carboxylic acids, ethylenically unsaturated carboxylic acids, ethylenically unsaturated epoxides, ethylenically unsaturated isocyanates, ethylene glycol di(meth)acrylate, trimethylolpropane tri(meth)acrylate, diethylene glycol di(meth)acrylate, divinyl benzene, triallyl cyanurate, allyl acrylate, diallyl phthalate, diallyl sucrose and combinations thereof.

10. The process of claim 8 wherein X is the residue of a tri- to -octa functional alcohol.

11. The process of claim 8 wherein X is a residue of glycerol, sorbitol, trimethylolpropane, pentaerythritol, dipentaerythritol, tripentaerythritol, and inositol.

12. A process for preparing a star polymer comprising:
   a) polymerizing a mercaptan core according to claim 1 and a first monomer mixture;
   b) adding to product of the polymerization step of part a) a second monomer mixture;
   c) polymerizing the second monomer mixture and the product of the polymerization step of part a).

13. A process according to claim 12 wherein X is the residue of a tri- to -octa functional alcohol.

14. A process according to claim 12 wherein X is a residue of glycerol, sorbitol, trimethylolpropane, pentaerythritol, dipentaerythritol, tripentaerythritol, and inositol.

15. The process of claim 12 wherein the first and second monomer mixtures are the same or different and are selected from the group consisting of the esters and amides of acrylic and methacrylic acids with alcohols, phenols and amines; the vinyl aromatic compounds, and substituted derivatives thereof; vinyl esters; vinyl amides, ethylenically unsaturated nitrites, hydroxyalkyl esters of ethylenically unsaturated carboxylic acids, ethylenically unsaturated carboxylic acids, ethylenically unsaturated epoxides, ethylenically unsaturated isocyanates, ethylene glycol di(meth)acrylate, trimethylolpropane tri(meth)acrylate, diethylene glycol di(meth)acrylate, divinyl benzene, triallyl cyanurate, allyl acrylate, diallyl phthalate, diallyl sucrose and combinations thereof.

* * * * *